US006114110A

United States Patent [19]
Nabel et al.

[11] Patent Number: 6,114,110
[45] Date of Patent: *Sep. 5, 2000

[54] ISOLATION AND PROPAGATION OF A HUMAN HERPESVIRUS DERIVED FROM AIDS-ASSOCIATED KAPOSI'S SARCOMA CELLS

[75] Inventors: Gary J. Nabel; Brian J. Nickoloff, both of Ann Arbor, Mich.

[73] Assignee: University of Michigan, Ann Arbor, Mich.

[ * ] Notice: Under 35 U.S.C. 154(b), the term of this patent shall be extended for 160 days.

[21] Appl. No.: 08/585,588

[22] Filed: Jan. 16, 1996

[51] Int. Cl.[7] .............................. C12Q 1/70; C12Q 1/68; G01N 33/53

[52] U.S. Cl. ................................. 435/5; 435/6; 435/7.1; 435/7.94; 435/41; 435/235.1

[58] Field of Search .......................... 435/5, 6, 7.1, 7.94, 435/41, 240.23, 235.1, 240.21, 91.2; 424/184.1, 130.1, 204.1, 277.1, 229.1

[56] References Cited

U.S. PATENT DOCUMENTS

| | | |
|---|---|---|
| 5,131,907 | 7/1992 | Williams et al. . |
| 5,723,125 | 3/1998 | Chang et al. . |
| 5,801,042 | 9/1998 | Chang et al. . |
| 5,830,759 | 11/1998 | Chang et al. . |
| 5,831,064 | 11/1998 | Chang et al. . |
| 5,834,599 | 11/1998 | Chang et al. . |
| 5,849,564 | 12/1998 | Chang et al. . |
| 5,853,734 | 12/1998 | Chang et al. . |
| 5,854,398 | 12/1998 | Chang et al. . |
| 5,854,418 | 12/1998 | Chang et al. . |
| 5,859,225 | 1/1999 | Chang et al. . |
| 5,861,500 | 1/1999 | Chang et al. . |
| 5,863,787 | 1/1999 | Chang et al. . |
| 5,882,644 | 3/1999 | Chang et al. . |

FOREIGN PATENT DOCUMENTS

WO 96/15779  5/1996  WIPO .

OTHER PUBLICATIONS

Altman, Virus Linked to a Cancer in AIDS Patients Is Identified, The New York Times, Mar. 1, 1996.
Ambroziak et al., Herpes–Like Sequences in HIV–Infected and Uninfected Kaposi's Sarcoma Patients, Science, 268: 582–583, 1995.
Apolloni et al., Detection of A–Type and B–Type Epstein–Barr Virus in Throat Washings and Lymphocytes, Virol., 202:978–981, 1994.
Ausubel et al., editors, Current Protocols in Molecular Biology, John Wiley & Sons, Inc., 1995.
Barillari et al., Effect of Cytokines from Activated Immune Cells on Vascular Cell Growth and HIV–1 Gene Expression, J. Immunol., 149: 3727–3734, 1992.
Benjamin et al., Human B–Cell Interleukin–10: B–Cell Lines Derived From Patients With Acquired Immunodeficiency Syndrome and Burkitt's Lymphoma Constitutively Secrete Large Quantities of Interleukin–10, Blood, 80: 1289–1298, 1992.

Beral et al., Cancer Surveys: Cancer, HIV and AIDS, Eur. J. Cancer., 27: 1057–1058, 1991.
Beral et al., Kaposi's sarcoma among persons with AIDS: a sexually transmitted infection?, Lancet, 335: 123–128, 1990.
Beral, Epidemiology of Kaposi's Sarcoma, Cancer Surv., 10: 5–22, 1991.
Boshoff et al., Kaposi's sarcoma–associated herpesvirus infects endothelial and spindle cells, Nature Medicine, 1: 1274–1278, 1995. Abstract only.
Browing et al., Identification and Culture of Kaposi's Sarcoma–Like Spindle Cells From the Pheripheral Blood of Human Immunodeficiency Virus–1–Infected Individuals and Normal Controls, Blood, 84: 2711–2720, 1994.
Cao et al., Rapid Detection of Cutaneous Herpes Simplex Virus Infection with the Polymerase Chain Reaction, J. Invest. Dermatol., 82: 391–392, 1989.
Cesarman et al., In Vitro Establishment and Characterization of Two Acquired Immunodeficiency Syndrome–Related Lymphoma Cell Lines (BC–1 and BC–2) Containing Kaposi's Sarcoma–Associated Herpesvirus–Like (KSHV) DNA Sequences, Blood, 86: 2708–2714, 1995.
Cesarman et al., Kaposi's Sarcoma–Associated Herpesvirus–Like DNA Sequences in AIDS–Related Body–Cavity–Based Lymphomas, N. Eng. J. Med., 332: 1186–1191, 1995.
Chadburn et al., CD30 (Ki–l) Positive Anaplastic Large Cell Lymphomas in Individuals Infected with the Human Immunodeficiency Virus, Cancer 72: 3078–3090, 1993.
Chang et al., Identification of Herpesvirus–Like DNA Sequences in AIDS–Associated Kaposi's Sarcoma, Science, 266: 1865–1869, 1994.
Coen, et al., Quantitation of rare DNAs by PCR. In: F.M. Ausubel, R. Brent, R.E. Kingston, D.D. Moore, J.G. Seidman, J.A. Smith and K. Struhl (eds.), Current Protocols in Molecular Biology, pp. 15.3.1–15.3.8, New York: Greene Publishing Associates and Wiley–Interscience. 1992.
Cohen, Controversy: Is KS Really Caused By New Herpesvirus?, Science, 268: 1847–1848, 1995.
Dambaugh et al., Epstein–Barr virus (B95–8) DNA VII: Molecular Cloning and detailed mapping, Proc. Natl. Acad. Sci. USA, 77:2999–3003, 1980.
Dupin et al., Herpesvirus–like DNA sequences in patients with Mediterranean Kaposi's sarcoma Lancet, 345: 761–762, 1995.
Eizuru et al., Application of "Hirt Supernatant" DNA to the Molecular Epidemiology of Cytomegalovirus Infections, J. Clin. Microbiol., 20: 1012–1014, 1984.

(List continued on next page.)

*Primary Examiner*—Ali Salimi
*Attorney, Agent, or Firm*—Brinks Hofer Gilson & Lione

[57] ABSTRACT

This present invention demonstrates the presence of a replication-competent herpesvirus associated with AIDS-associated Kaposi's sarcoma cells, vaccines derived therefrom, methods for diagnosing for Kaposi sarcoma, and methods for screening for antiviral drugs effective against human herpesvirus.

12 Claims, 3 Drawing Sheets

OTHER PUBLICATIONS

Ensoli et al., Cytokines and Growth Factors in the Pathogenesis of AIDS–Associated Kaposi's Sarcoma, Immunodol. Rev., 127:147–155, 1992.

Ensoli et al., Synergy between basic fibroblast growth factor and HIV–1 Tat protein in induction of Kaposi's sarcoma, Nature, 371: 674–680, 1994.

Finesmith et al., Kaposi's Sarcoma, Int. J. Dermatol., 33: 755–762, 1994.

Gail et al., Projections of the Incidence of Non–Hodgkin's Lymphoma Related to Acquired Immunodeficiency Syndrome, J. Natl. Cancer Inst., 83: 695–701, 1991.

Gill et al., AIDS–Related Malignant Lymphoma: Results of Prospective Treatment Trials, J. Clin. Oncol., 5: 1322–1328, 1987.

Goldschmidts et al., Epstein–Barr Virus Genotypes in AIDS–Associated Lymphomas are Similar to those in Endemic Burkitt's Lymphomas, Leukemia, 6: 875–878, 1992.

Green et al., Primary Lymphomatous Effusion in AIDS: A Morphological, Immunophenotypic, and Molecular Study, Modern Pathol., 8: 39–45, 1995.

Hammerling et al., editors, in Monoclonal Antibodies and T Cell Hybridomas, Elsevier, NY, 1981.

Harlow and Lane, Antibodies, A Laboratory Manual, Cold Spring Harbor Laboratory Press, NY, 1988.

Herndier et al., Acquired Immunodeficiency Syndrome–Associated T–Cell Lymphoma: Evidence for Human Immunodeficiency Virus Type 1–Associated T–Cell Transformation, Blood, 79: 1768–1774, 1992.

Huang et al., Cultured Kaposi's Sarcoma Cell Lines Express Factor XIIIa, CD14, and VCAM–1, but Not Factor VIII or ELAM–1, Arch. Dermatol., 129: 1291–1296, 1993.

Huang et al., Human herpesvirus–like nucleic acid in various forms of Kaposi's sarcoma, Lancet, 345: 759–761, 1995.

Ioachim et al., Kaposi's Sarcoma of Internal Organs, A Multiparameter Study of 86 Cases, Cancer, 75: 1376–1385, 1995.

Jaffe, Culture and identification of large vessel endothelial cells. In: E.A. Jaffe (ed.), Biology of Endothelial Cells, pp. 1–13, the Hague: Martinus Nijof. 1984.

Knowles et al., Molecular Genetic Analysis of Three AIDS–Associated Neoplasms of Uncertain Lineage Demonstrates Their B–Cell Derivation and the Possible Pathogenetic Role of the Epstein–Barr Virus, Blood, 73: 792–799, 1989.

Kohler et al., Continuous cultures of fused cells secreting antibody of predefined specificity, Nature, 256: 495–497, 1975.

Kohler et al., Derivation of specific antibody–producing tissue culture and tumor lines by cell fusion, Eur. J. Immunol., 6: 511–519, 1976.

Kohler et al., Fusion between immunoglobulin–secreting and nonsecreting myeloma cell lines, Eur. J. Immunol., 6: 292–295, 1976.

Lane, A Shor–Duration Polyethylene Glycol Fusion Technique for Increasing Production of Monoclonal Antibody–Secreting Hybridomas, J. Immunol. Methods, 181: 223–228, 1985.

Langone, et al., editor, Methods of Enzymology, vol. 73, Immunochemical Techniques Part B, Academic Press, 1981.

Lebbe et al., Kaposi's sarcoma, and new herpesvirus, Lancet, 345: 1180, 1995.

Levine et al., Human Immunodeficiency Virus–Related Lymphoma: Prognostic Factors Predictive of Survival, Cancer, 68: 2466–2472, 1991.

Levy, A new human herpesvirus: KSHV or HHV8?, Lancet, 34: 786, 1995.

Manthorpe et al., Gene Therapy by Intramuscular Injection of Plasmid DNA: Studies on Firefly Luciferase Gene Expression in Mice, Hum. Gene Ther., 4: 419–431, 1993.

Marsh et al., Cytokine Expression in Large Cell Lymphoma Associated with Acquired Immunodeficiency Syndrome, J. Interferon Cytokine Res., 15: 261–268, 1995.

Moore et al., Detection of Herpesvirus–Like DNA Sequences in Kaposi's Sarcoma in Patients With and Those Without HIV Infection, N. Eng. J. Med., 332: 1181–1185, 1995.

Naidu et al., Role of scatter factor in the pathogenesis of AIDS–related Kaposi's sarcoma, Proc. Natl. Acad. Sci. USA, 91: 5281–5285, 1994.

Nair et al., Identification of a Major Growth Factor for AIDS–Kaposi's Sarcoma Cells as Oncostatin M, Science, 255: 1430–1432, 1992.

Nakamura et al., Kaposi's sarcoma cells: long–term culture with growth factor from retrovirus–infected CD4+ T cells, Science, 242: 426–430, 1988. Abstract only.

Ng et al., IgMs Produced by Two Acquired Immune Deficiency Syndrome Lymphoma Cell Lines: Ig Binding Specificity and $V_H$–Gene Putative Somatic Mutation Analysis, Blood, 83: 1067–1078, 1994.

Nickoloff et al., Factor XIIIa–Expressing Dermal Dendrocytes in AIDS–Associated Cutaneous Kaposi's Sarcomas, Science, 243: 1736–1737, 1989.

Palmer, E.L. and Martin, M.L., Electron Microscopy in Viral Diagnosis, CRC Press, Boca Raton, Florida, 1988.

Pater et al., Isolation of Herpes Simplex Virus DNA from the "Hirt Supernatant", Virol., 75: 481–483, 1976.

Reene et al., Lytic growth of Kaposi's sarcoma–associated herpesvirus (human herpesvirus 8) in culture, Nature Medicine, 2: 342–346, 1996.

Rutgers et al., The Expression of Endothelial Cell Surface Antigens by AIDS–Associated Kaposi's Sarcoma, Evidence for a Vascular Endothelial Cell Origin, Am. J. Pathol., 122: 493–499, 1986.

Sa'Adu et al., Lymphotropic viruses in 'common variable' immunodeficiency—PCR analysis of lymphocyte DNA for HIV–1 and HHV–6, Clin. Exp. Immunol., 91: 50–53, 1993.

Safai et al., The Natural History of Kaposi's Sarcoma in the Acquired Immunodeficiency Syndrome, Ann. Intern. Med., 103: 744–750, 1985.

Samaniego et al., Inflammatory Cytokines Induce AIDS–Kaposi's Sarcoma–Derived Spindle Cells to Produce and Release Basic Fibroblast Growth Factor and Enhance Kaposi's Sarcoma–Like Lesion Formation in Nude Mice, J. Immunol., 154: 3582–3592, 1995.

Sambrook et al., Molecular Cloning, A Laboratory Manual, Cold Spring Harbor Laboratory Press, NY, 1989.

Scharf et al., Direct Cloning and Sequence Analysis of Enzymatically Amplified Genomic Sequences, Science, 233: 1076–1078, 1986.

Shiramizu et al., Molecular and Immunophenotypic Characterizaion of AIDS–Associated, Epstein Barr Virus–Negative, Polyclonal Lymphoma, J. Clin. Oncol., 10: 383–389, 1992.

Stein et al., AIDS–related Kaposi's sarcoma: a review, Isr. J. Med. Sci., 30: 298–305, 1994. Abstract only.

Straus et al., Herpes Simplex Virus Infection: Biology, Treatment, and Prevention, Ann. Int. Med., 103: 404–419, 1985.

Van Vunakis, et al., editor, Methods of Enzymology, vol. 70, Immunochemical Techniques Part A, Academic Press, 1980.

Walts et al., Diagnosis of Malignant Lymphoma in Effusions from Patients with AIDS by Gene Rearrangement, Am. J. Clin. Pathol. 94: 170–175, 1990.

Weiss, Human herpesvirus 8 in lymphoma and Kaposi's sarcoma: Now the virus can be propagated, Nature Medicine, 2: 277–278, 1996.

Whitby et al., Detection of Kaposi's sarcoma associated herpesvirus in peripheral blood of HIV–infected individuals and progression ot Kaposi's sarcoma, Lancet, 346: 799–802, 1995.

Wilson et al., Recent developments in the periodate method of conjugating horseradish peroxidase (HRPO) to antibodies, pp. 215–224, in Knapp et al., eds., Immunofluorescence and Related Staining Techniques, Elsevier/North Holland Biomedical Press, Amsterdam, 1978.

Yang et al., Regulation of Adhesion Molecule Expression in Kaposi's Sarcoma Cells, J. Immunol., 152: 361–373, 1994.

ISOLATION AND PROPAGATION OF A HUMAN HERPESVIRUS DERIVED FROM AIDS-ASSOCIATED KAPOSI'S SARCOMA CELLS

This work was supported in part by grants from the National Institutes of Health.

BACKGROUND OF THE INVENTION

1. Field of the Invention

The present invention relates to the isolation and propagation of a novel human herpesvirus derived from AIDS-associated Kaposi's Sarcoma cells, diagnostic methods using the same, methods for screening for anti-viral drugs using the same and vaccines against Kaposi's Sarcoma.

2. Discussion of the Background

Kaposi's sarcoma (KS) was originally described in the late 1800's as a rare and relatively benign neoplasm of elderly men of Jewish or Mediterranean descent. Today, KS is recognized as the most common malignancy in AIDS patients, affecting approximately 20% of human immunodeficiency virus-1 (HIV-1)-positive patients (1–3). AIDS-related KS (also known as epidemic KS) is clinically more aggressive than other forms of KS, including classical (Mediterranean), African (endemic), and iatrogenic immunosuppressive-drug associated with organ transplantation [reviewed in (4,5)]. While often presenting in the skin of HIV-1 positive patients, AIDS-KS lesions can involve internal organs, particularly the lungs and gastrointestinal tract, resulting in severe and potentially fatal hemorrhagic disease (6).

KS is characterized histologically by a proliferation of spindle-shaped tumor cells mixed with endothelial cells forming blood vessels (angiogenesis), fibroblasts, dermal dendrocytes, and an inflammatory cell infiltrate (7). The origin of the spindle-shaped KS tumor cells has been difficult to define with certainty, but is thought to derive from either endothelial or vascular smooth muscle cells (8–11). In addition, a variety of immune or inflammatory cytokines and oncogenes or viral proteins have been found in association with these lesions (11–15). While the etiologic agent causing KS is unclear, epidemiological data has suggested that an infectious agent could potentially spread the disease through sexual contact (16). Although several viruses, including cytomegalovirus, hepatitis B virus, and human papillomavirus were found in KS patients, no single agent was found consistently in all patient lesions until recently when Chang, Moore, and colleagues demonstrated that over 90% of AIDS-KS tissue samples were positive for herpesvirus-like DNA sequences (17). These DNA sequences were homologous to, but distinct from, minor capsid and tegument proteins of Epstein-Barr virus (EBV) and herpesvirus saimiri (17), and defined a putative new member of the gammaherpesvirus family which is currently referred to as KS-associated herpesvirus, KSHV, or human herpesvirus 8, HHV-8. Since then, several different laboratories have demonstrated the presence of this viral sequence in tissue from KS patients with classic, African endemic and AIDS-associated KS (18–20) as well as patients with body-cavity-based lymphomas (21,22).

It has remained uncertain, however, whether this new herpesvirus was replication-competent or represented a replication-defective, adventitious virus present in KS tissue. To date, although the presence of this virus has been noted in B lymphoma cells which also contain EBV, it has not been possible to demonstrate viral replication in vitro.

Since the publication of a DNA sequence associated with Kaposi sarcoma, several reports have either supported (18–20,23–25) or refuted (26,27) the notion that this novel DNA virus was important in KS. To date, it had not been possible to propagate this putative virus or even to maintain it in cell culture in the absence of other known herpesviruses, making it difficult to characterize its transmissibility and its host cell range, and to develop anti-viral and diagnostic reagents.

It is therefore desirable to isolate intact human herpesvirus from Kaposi's sarcoma cells and to propagate the same in vitro. The earliest studies in this field defined a novel viral DNA sequence associated with Kaposi's sarcoma lesions (Chang et al., Science (1994) 266:1865–1869). Although the sequence suggested that it was a member of the gamma herpesvirus family, it has not been possible to address the question of whether this represents a true replicating virus or a helper virus associated with another pathogen that might cause the disease. More recently, the presence of the virus DNA sequence was noted in a B cell lymphoma in a persistent form (22). Unfortunately, this line contained a second herpesvirus, EBV, which did not allow definitive isolation or identification of the KS-associated virus. In addition, it did not provide a means to replicate or propagate the virus which was carried in these cells but could not be amplified. The ability now to propagate and clone this virus allows specific diagnostic tests to be developed, by allowing the definition of the full range of the DNAs, RNAs and proteins in the native virus, by permitting the generation of antibodies to diagnose the virus, and by providing a means to establish its epidemiologic association with the disease. It also establishes a method to generate a prototype virus which may be useful for the development of a vaccine to prevent this disease. This isolation of this virus will also make it possible to fulfill Koch's postulates in animal models, showing that it can transmit the genetic information which causes the disease. Finally, it provides a critical assay system for the replication of the virus and allows for large scale screening of antiviral compounds that inhibit viral replication in vitro. Without the ability to replicate the virus, these goals could not be achieved. The present invention provides a method to establish and propagate replication-competent virus which will make these goals possible and likely to succeed. It thus represents a major advance in the field which was not obvious and was widely recognized as needed.

SUMMARY OF THE INVENTION

Accordingly, one object of this invention is to provide a method for cultivating KS tumor cells that contain HHV-8 virus in a nonreplicative state.

A second object of the present invention is to provide an intact human herpesvirus derived from AIDS-associated Kaposi's Sarcoma cells (HHV-8).

A third object of the present invention is to provide methods for propagating human herpesvirus derived from AIDS-associated Kaposi's Sarcoma cells in vitro.

A fourth object of the present invention is to provide diagnostic methods for detecting human herpesvirus derived from AIDS-associated Kaposi's sarcoma cells in a patient.

A fifth object of the present invention is to provide methods for screening for antiviral drugs using cells infected with human herpesvirus derived from AIDS-associated Kaposi's sarcoma cells.

The present inventors have now achieved these and other objects by isolating human herpesvirus and discovering methods for propagating the same. The present inventors utilized growth conditions that allow multiple passages of primary KS cell lines. KSHV, or HHV-8, DNA sequences were detected in early passages of these tumor cells which were nearly identical to the previously described herpes-like DNA sequences (17,19). By co-culture with the human embryonal kidney epithelial cell line, 293 cells, cell-free viral lysate was isolated which induced a cytopathic effect on 293 cells. Characterization of the virus was performed, and propagation by serial passage was confirmed.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1A:
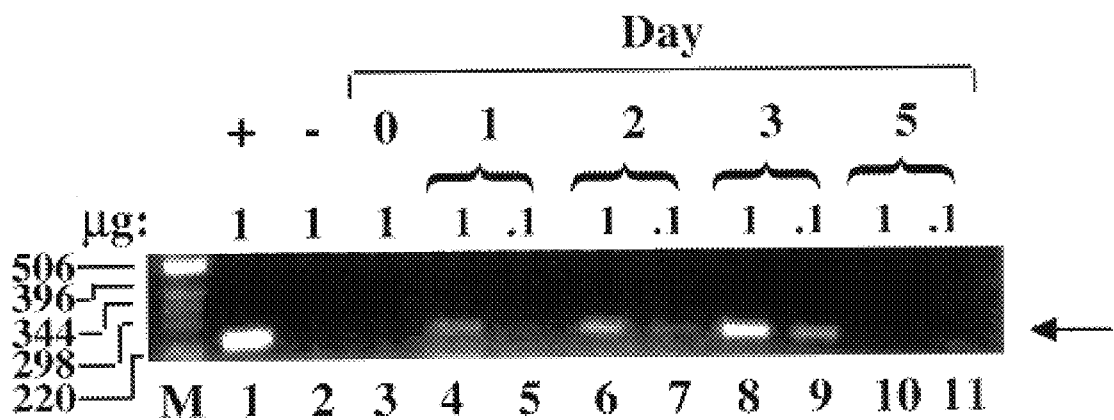
FIG. 1. Detection of viral DNA sequences in 293 cell initially co-cultured with KS cells and subsequently serial passage of virus.

Cultivation of Kaposi's Sarcoma Cells that Contain HHV-8 Virus in a Nonreplicative State The method of cultivating KS cells according to the present invention comprises the steps of:

isolating a KS cell from a KS lesion or tissue taken from a patient biopsy; and culturing said KS cell on a media coated with endothelial cell attachment factor.

KS cells can be isolated from tissue taken from a patient biopsy or, preferably, from KS lesions of the skin from HIV-positive patients. These cells can be plated on tissue culture dishes coated with microvascular endothelial cell attachment factor and maintained in RPMI media supplemented with L-glutamine, heparin, appropriate antibiotics (preferably penicillin, streptomycin and gentamicin), serum (preferably heat inactivated fetal bovine serum) and growth factors (preferably endothelial cell growth supplement). Suitable serum concentrations are 0–20%. Cells can suitably be grown at a temperature range of from 35 to 40° C. (preferably 37–38° C.) in a $CO_2$ incubator (preferably in an atmosphere containing 2–5% $CO_2$). Cells are allowed to reach confluency. KS cells can be removed from confluent tissue cultures using conventional procedures such as exposure to trypsin and EDTA.

The present method differs from conventional methods which did not incorporate endothelial cell attachment factor or endothelial cell growth factor (See Nakamura et al, Science 242:430–433 (1988)).

Intact Human Herpesvirus 8 (HHV-8)

HHV-8 can be isolated from KS cells. Alternatively, HHV-8 can be isolated from co-cultures of KS cells and cells of epithelial or umbilical endothelial origin. Suitable epithelial and umbilical endothelial cells are disclosed below. Any ratio of KS cells to cells of renal epithelial or umbilical endothelial origin can be used. Preferably 1:10 KS cells to cells of renal epithelial or umbilical endothelial origin can be used. Cells are co-plated onto media, optionally in the presence of growth factors such as TNF-a and allowed to reach confluency.

DNA can be isolated from the above tissue culture cells as previously described (28). Briefly, the cells are washed in phosphate-buffered saline and gently lysed at room temperature. The solution is then centrifuged and the resulting supernatant treated with an enzyme such as pronase. The DNA is then extracted, precipitated, washed and dried. Isolated DNA is then amplified.

The DNA is then ligated into a suitable expression vector such as lambda gt10 or gt 11, Bluescript or SuperCos1 (Stratagene).

293 cells infected with HHV-8 have been deposited in accordance with the Budapest Treaty with the American Type Culture Collection, 12301 Parklawn Drive, Rockville Md. 20852 on Jan. 7, 1998 under accession no. VR-2595.

Novel Methods for Propagating Human Herpesvirus

Human herpesvirus derived from AIDS-associated Kaposi's sarcoma cells can be propagated in cells of epithelial or umbilical endothelial origin. Unlike previous methods, the method of the present invention propagates cells infected with HHV-8 in the absence of HTLV-II conditioned media. The method of the present invention comprises:

contacting a culture of epithelial cells or umbilical endothelial cord cells with cells or cell lysate of a human herpesvirus derived from Kaposi's sarcoma cell to form an infected cell culture, incubating the infected cell culture for at least 1 day in the presence of endothelial cell attachment factor, and passaging the infected cell culture.

Suitable epithelial cells can be derived from adult or, preferably embryonic sources. Suitable epithelial and umbilical endothelial cells can be derived from primates or, preferably, human sources. Preferred epithelial cells are renal epithelial cells. For example, 293 cells, which are human embryonal kidney epithelial cells can be used. 293 cells are available from the American Type Culture Collection. Embryonic epithelial or umbilical endothelial cells can be infected with human herpesvirus using known methods 3 to 24 hours after seeding. Suitable inoculum includes virally infected KS cells or viral lysates. The concentration of inoculum is preferably at least $10^{-6}$.

The infected cell culture can be incubated at 35–60° C. in relevant media in a humidified atmosphere and appropriate $O_2$ and $CO_2$ concentrations.

The virus can be serially passaged using methods known in the art. Briefly, cells infected with the virus are lysed and cell lysates are contacted with uninfected cells.

Passaging is conducted after at least three days of infection. Infected cells are characterized by the presence of multinucleated giant cells, nuclear molding and dissolution of chromatin with residual chromatin marginating along the nuclear membrane. Within 5 days after infection, virtually all of the cells undergo necrosis with condensation of chromatin and other morphological changes consistent with apoptosis.

Alternatively, HHV-8 can be propagated less efficiently using methods known in the art.

Vaccines Derived from Human Herpesvirus

Virus can suitably be harvested from cell culture when the maximal cytopathic effect is observed. Observation of cytopathic effect in cell cultures can be endpoint determined up to 5 days; this can suitably be done by visual evaluation of morphological changes on the monolayer or by fluorescent antibody staining techniques.

Suitable harvest methods include: agitation, aspiration, scraping, or freeze thawing accompanied by aspiration. Preferably, harvested viruses are stored at −70°C.

The activity of the virus can be suitably measured quantitatively by preparing dilutions of the sample and determining the highest dilution (endpoint) at which activity is still detectable. The preferred method is the Reed Muench method which permits interpretation of the 50% endpoint from data derived from a quantal response. The formula can be applied similarly to rates of infection in any host system. The unit of infectivity used to express the results are mean embryo infective dose, $EID_{50}$, and mean tissue culture infective dose, $TCID_{50}$.

Vaccines can be produced from the harvested virus and viral lysates using techniques known in the art.

Diagnostic Methods for Detecting Kaposi's Sarcoma Cells

Antibodies to the intact human herpesvirus can be generated using methods known in the art (see for example, chapter 18 of Sambrook et al, "Molecular Cloning: A Laboratory Manual", 2nd ed., Cold Spring Harbor Laboratory Press, N.Y., 1989).

Antibodies, preferably polyclonal, against the intact virus can be used in Western blot tests to determine the presence or absence of human herpesvirus shed from Kaposi's sarcoma cells in a biological sample such as blood, semen or urine. Western blot analysis can be conduct using methods well known in the art.

Methods for Screening for Antiviral Drugs

Cells infected with human herpesvirus derived from Kaposi's sarcoma cells can be used to screen for antiviral activity. The method of the present invention comprises, contacting an antiviral drug candidate with a newly infected cell (within 2 to 24 hours following infecting), culturing the infected cell and determining the effect of the antiviral drug candidate.

The effect of the antiviral drug can be determined by comparing cytopathicity of untreated infected cells with treated infected cells. If treated infected cells persist for at least 7 days, preferably at least 10 days, the drug has antiviral activity against human herpesvirus derived from Kaposi's sarcoma cells.

Alternatively, screening can be performed using ELISA, RIA or other methods of immune detection known in the art to detect decreased production of specific viral gene products in the presence of the antiviral drug. These tests could screen directly for antigens an immunoprecipitate. Alternatively, the immune response of the patient to an antigen can be screened using a western blot assay.

EXAMPLES

Having generally described this invention, a further understanding can be obtained by reference to certain specific examples which are provided herein for purposes of illustration only and are not intended to be limiting unless otherwise specified.

Cell Culture

Human KS cells were isolated independently from KS lesions of the skin from five different HIV-positive patients (designated KS#1–8) through mechanical disruption and enzymatic digestion of biopsies as previously described (29). In contrast to previous reports which used an HTLV-II conditioned media, alternative media and culture conditions for these experiments were developed. The cells were plated on tissue culture dishes (Corning, Corning, N.Y.) coated with microvascular endothelial cell attachment factor (Cell Systems, Kirkland, Wash.) and were maintained in RPMI 1640 and 20% heat inactivated fetal bovine serum (FBS) supplemented with 10% Nutridoma HU (Boehringer Mannheim Biochemicals, Indianapolis, Ind.), 2 mM L-glutamine, 100 units/ml penicillin, 100 mg/ml streptomycin, 50 mg/ml gentamicin, 50 mg/ml endothelial cell growth supplement (ECGS, ICN Biochemicals, Aurora, Ohio) and 16 units/ml bovine heparin. Isolated KS tumor cells were characterized by immunohistochemistry as stated in the text (29,30). Human umbilical vein endothelial cells (HUVECs) were isolated by collagenase treatment of freshly obtained human umbilical cords and plated on gelatin-coated tissue culture dishes (31). RPMI-1640 containing 20% heat inactivated FBS supplemented with 2 mM L-glutamine, 100 units/ml penicillin, 100 mg/ml streptomycin, 50 mg/ml gentamicin, 50 mg/ml ECGS (Collaborative Research, Bedford, Mass.) and 16 units/ml bovine heparin was used to maintain the cells. HUVECs were characterized by a cobblestone appearance and specific staining for von Willebrand factor. The transformed human embryonal kidney cell line, 293, was provided by Dr. Garry Nolan, and the cells were maintained in Dulbecco's modified Eagle's media containing 10% heat inactivated FBS, 2 mM L-glutamine, 100 units/ml penicillin, and 100 mg/ml streptomycin.

Electron Microscopy

KS cells were removed from confluent tissue culture dishes using brief exposure to 0.03% trypsin and 0.01% ethylenediaminetetraacetic acid (EDTA). The cells were pelleted and resuspended in 50% gluteraldehyde and 0.1M cacodylate buffer. Alternatively, the confluent monolayers of cells were fixed with gluteraldehyde and cacodylate buffer and removed from the plate by gently scrapping with a rubber policeman. The fixed cells were embedded, sectioned and stained for electron microscopy by the departmental electron microscopy core facility.

Figure 1B:
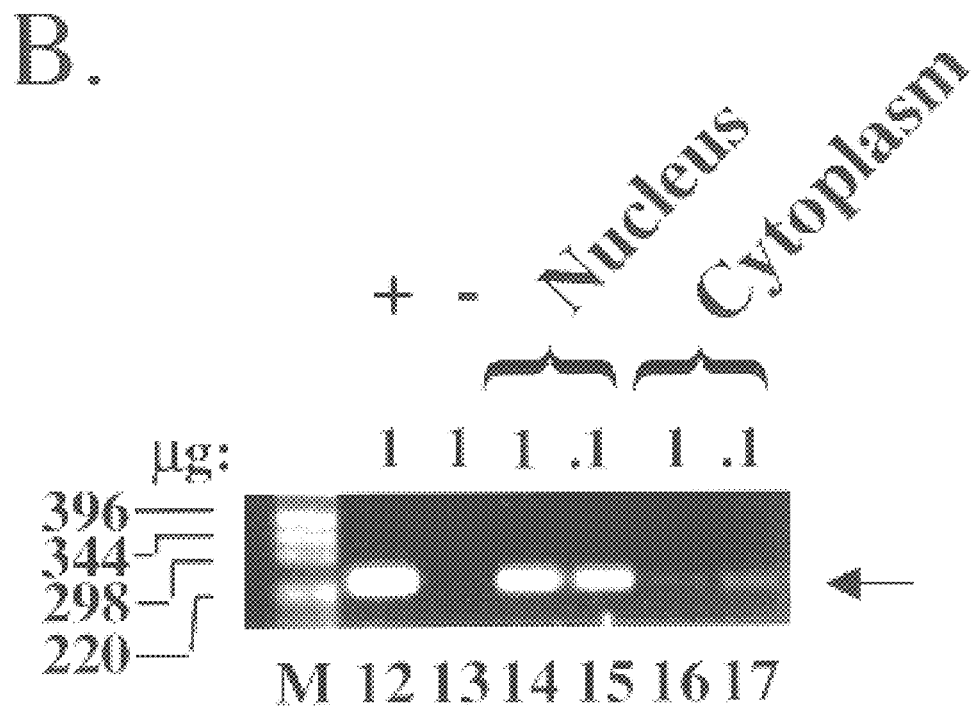

KS tumor cells in confluent areas demonstrated loss of contact inhibition by forming large spherules on the dish (FIG. 1A) adjacent to the epithelial appearing microvascular endothelial cells and, on subsequent passage, only the spindle-shaped cell continued to proliferate (FIG. 1B). It should be noted that despite several years and much experience in growing KS cells using previously published methodology, no such prolific population of tumor cells has previously been seen. A representative herpes-like virus particle detected in the cytoplasm of passage 2 KS cells is shown (FIG. 1B, inset).

DNA Isolation and Preparation of Hirt Supernatants

DNA was isolated from tissue culture cells as previously described (28). For isolation of DNA from paraffin-embedded sections, the tissue from 50 five-micron sections was dewaxed twice with xylene, washed twice with ethanol and dried before addition of the digestion buffer. To selectively isolate low molecular weight DNA, Hirt supernatants were prepared as previously described (32,33). Briefly, the cells were washed five times in phosphate-buffered saline (pH 7.0) and gently lysed for 15 minutes at room temperature in lysing solution (0.01M Tris (pH 8.0), 0.6% SDS, 0.01M EDTA). Sodium chloride was added for a final concentration of 1M and the mixture was incubated at 4° C. overnight. The solution was centrifuged at 17,000 ×g for one hour at 4° C., and the resulting supernatant treated with 1 mg/ml pronase at 37° C. for 3–4 hours. The DNA was extracted three times with equal volumes of buffer saturated phenol and precipitated with 2 volumes of isopropanol and ¹⁄₁₀ volume of 3M sodium acetate at −20° C. The precipitated DNA was washed successively with cold ethanol at 70%, 90% and 100%. The DNA was dried and resuspended in Tris/EDTA (TE) buffer.

Polymerase Chain Reaction

Isolated DNA was amplified by PCR using primers designed from the specific herpesvirus-like DNA sequence (17). The primers were 5'-AGC CGA AAG GAT TCC ACC ATT GTG CTC-3' (SEQ ID NO.:1) and 5'-TCC GTG TTG TCT ACG TCC AGA CGA TAT-3' (SEQ ID NO.:2). PCR reaction mixtures (50 ml volume) were set up containing 0.1 mg and 1 mg of isolated DNA, 50 pmol of each primer, 200 mM of each deoxynucleotide triphosphate, 1.5 mM magnesium chloride, 50 mM KCl, 20 mM Tris-HCl (pH 8.4) and 2.5 units of Taq DNA polymerase. DNA was amplified as follows: 94° C. for 3 minutes (1 cycle), 94° C. for 30 seconds, 72° C. for 2 minute (40 cycles), 72° C. for 10 minutes (1 cycle). PCR products were electrophoresed through a 2% agarose gel containing ethidium bromide. Successful PCR amplification with the herpesvirus-like DNA primers results in a single band at approximately 233 base pairs which is positioned at base pairs 987–1219 in the sequence published by Chang et al (17). Positive control DNA was isolated from a biopsy of pulmonary KS. PCR for human herpesvirus 6 (HHV-6), EBV, herpes simplex virus 1 and 2 (HSV 1 and 2) was performed using previously described primers and amplification conditions (34–36). CMV was detected using the following primers derived from the intron of the immediate early −1 gene under standard conditions: (sense) 5' CCA AGC TTC CAC GCT GTT TTG ACC TCC ATA GA 3' (SEQ ID NO.:3); (antisense) 5' CCA AGC TTC TGT CAG CTA TTA TGT CTG GTG GC 3' (SEQ ID NO.:4), generating a 908 bp product. Positive controls for these viruses were obtained from paraffin embedded tissue samples or from the EBV transformed B-cell line, M16B. For critical samples, the DNA was isolated and PCR reactions were performed independently by two investigators (KEF and JF) in separate laboratories.

DNA Cloning and Sequencing

DNA from isolated KS cells was amplified using PCR as described. 5:1 of the PCR product was electrophoresed through a 2% agarose gel containing ethidium bromide to demonstrate successful amplification. The PCR product was then ligated into a pCRII Vector according to the manufacturer's instructions (TA Cloning Kit, Invitrogen, San Diego, Calif.). Sequencing was performed using dideoxy (Sanger) sequencing and the Sequenase kit (United States Biochemical, Cleveland, Ohio). Sequencing of PCR products was performed at least two times to confirm the results.

Isolation of Virus from Co-Cultures

Early passage KS cells were plated in 6-well dishes coated with microvascular endothelial cell attachment factor and allowed to grow 50–70% confluence. Primary KS cells ($2 \times 10^5$ cells, passage 2–3) were removed from primary culture and incubated with 293 cells ($2 \times 10^6$), in 35 mm 6-well Costar plates in the presence or absence of TNF-a (200 IU/ml). Cell lysates were prepared by three cycles of freeze-thawing after 3–5 days and incubated at different dilutions with 293 cells in the absence of TNF-a. For serial propagation, half of the cell culture was used to prepare lysates at day 3 post-infection, while the remainder of the cell culture was maintained to confirm subsequent cytopathic effect CPE. PCR positivity was confirmed in the cell lysate. Virus was propagated serially for at least 5 passages. Estimation of titer was made by incubation of lysates at progressive dilutions ($10^{-2}$–$10^{-10}$) with 293 or other target cells.

Viral DNA was detected by PCR in Hirt supernatants of 293 cells at the indicated times after infection (FIG. 1A) and with DNA isolated from the indicated enriched subcellular fractions (FIG. 1B). The arrow denotes the specific 233 bp DNA fragment. (+) represents a positive control sample from KS lesion, (−) represents uninfected 293 cell DNA.

Figure 2:
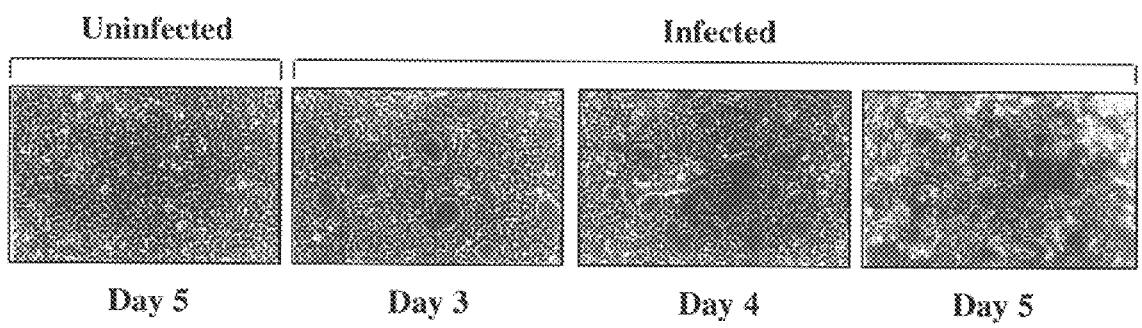
FIG. 2. 293 cells from control (uninfected) or those exposed to cell-free viral lysates (infected) for the indicated number of days in vitro before analysis by phase contrast microscopy. (Magnification: ×10).

FIG. 2 is a phase contrast microscopy (Magnification: ×10) of a cell.

RESULTS

Culture and Characterization of Isolated KS Cells

Cell culture conditions were developed which did not require the presence of HTLV-II conditioned media as used in previous studies. Under these conditions, KS cell lines grew rapidly after initiation of culture. Initially, macroscopic clusters of cells were observed which appear to contain both epithelioid-appearing endothelial cells and spindle-shaped mesenchymal cells (FIG. 1A). Subsequently, after the first passage, spindle-shaped cells characteristic of KS were observed, whose doubling times ranged from 24–48 hours (FIG. 1B). Each KS spindle cell line was positive for factor XIIIa and VCAM-1 by immunohistochemical staining, and negative for factor XIIIs, E-selectin, PECAM-1 (CD31), factor VIII, and CD34. Expression of these markers was not altered by IFN-g or TNF-a stimulation. These results are consistent with previously published data on the phenotype of isolated KS cells using different culture conditions (9,29).

Detection of Herpesvirus-like DNA in KS Cells

PCR was used to determine whether the proliferating KS cells contained recently described herpesvirus-like DNA sequences (17). 75% (6 of 8 isolates) of early passage, isolated KS tumor cells were positive for this DNA sequence using PCR (Table 1).

TABLE 1

| | Probe | | | | | |
|---|---|---|---|---|---|---|
| Sample | KS herpesvirus | HHV-6 | HSV1&2 | EBV-A | EBV-B | CMV |
| Isolated KS cells | | | | | | |
| KS-1 | Negative | Negative | Negative | Negative | Negative | Negative |
| KS-2 | Positive | Negative | Negative | Negative | Negative | Negative |
| KS-3 | Positive | Negative | Negative | Negative | Negative | Negative |
| KS-4 | Positive | Negative | Negative | Negative | Negative | Negative |
| KS-5 | Positive | Negative | Negative | Negative | Negative | Negative |
| KS-6 | Positive | Negative | Negative | Negative | Negative | Negative |
| KS-7 | Negative | Negative | Negative | Negative | Negative | Negative |
| KS-8 | Positive | ND | ND | ND | ND | Negative |
| Patient Samples | | | | | | |
| Pulmonary KS A | Positive | Positive | Negative | Negative | Negative | Negative |
| Pulmonary KS B | Positive | Positive | Negative | Negative | Negative | Negative |
| Psoriasis | Negative | Negative | ND | ND | ND | Negative |

TABLE 1-continued

| Sample | Probe | | | | | |
| --- | --- | --- | --- | --- | --- | --- |
| | KS herpesvirus | HHV-6 | HSV1&2 | EBV-A | EBV-B | CMV |
| Controls | | | | | | |
| HUVECs | Negative | Negative | Negative | Negative | Negative | Negative |
| 293 | Negative | Negative | Negative | Negative | Negative | Negative |

DNA was isolated from the indicated cell lines, and tissue samples were analyzed by PCR. Positive or negative indicates the presence or absence of relevant size fragment by ethidium bromide staining on agarose gels. Positive control reactions for each virus type were performed using an equal concentration (1:g) of DNA as in the test reactions.
*ND indicates not determined.

The signal was present in the cell lines until passage 2 or 3, and was then no longer detectable. The 233 bp PCR product was also found in DNA isolated from two separate paraffin embedded tissue samples obtained from a patient with pulmonary KS, as previously described in other patients (17,18). No evidence of KS-associated herpesvirus DNA sequences was detected in samples from isolated HUVECs, 293 cells, or DNA isolated from paraffin-embedded tissue from a psoriasis patient (Table 1). To determine if other herpesviruses might be present in these samples, PCR analysis was performed to detect HHV-6, HSV-1 and -2, CMV, EBV. DNA derived from these isolated KS cells were negative for each of these viral sequences (Table 1). Analysis of the 233 bp PCR product revealed a sequence identical to the herpesvirus-like DNA sequence originally reported by Chang and colleagues (17), with the exception of a single bp change (C to T) at codon 47, a substitution reported subsequently in seven KS patients (19).

Isolation of Lytic Virus

KS cells were co-cultured with a variety of other cell types for two to seven days. Cell-free lysates were prepared and tested for the presence of viral DNA by PCR. Consistently strong PCR signals were found on day two in DNA isolated from co-cultures with 293 cells while DNA from co-cultures with other cell types were largely negative (Table 2A).

TABLE 2A

| Sample | Description | PCR Positivity |
| --- | --- | --- |
| YPE | swine ECs | – |
| YSM | swine smooth muscle cells | – |
| HSM | human smooth muscle cells | – |
| HUVEC | human umbilical vein ECs | +/– |
| HDMEC | human microvascular ECs | – |
| H9 | human T-leukemia | – |
| CEM | human T-leukemia | – |
| Jurkat | human T-leukemia | – |
| MT-4 | human T-leukemia | – |
| HL-60 | human myelomonocytic leukemia | – |
| U937 | human promonocytic leukemia | – |
| HELA | human cervical carcinoma | – |
| 293 | human embryonal kidney cell | + |
| CaSki | HPV-16 positive epithelial cell | – |
| M16B | human B-cell infected with EBV | – |

In addition, the PCR signal in 293 cells was detected as the KS cells were lost from the culture (days 4–5). These findings suggested that the positive PCR signals were likely due to viral replication rather than persistence of DNA sequences from the primary KS cell line. In addition, greater cytopathicity was detected when KS and 293 co-cultures were incubated with TNF-a (Table 2B; see also FIG. 3).

TABLE 2B

| B. Cell Activation | | | |
| --- | --- | --- | --- |
| Cell | Stimulus | PCR Positivity | CPE |
| 293 | none | + | + |
| | IL-1 | — | — |
| | IL-6 | — | — |
| | TNF-a | +++ | +++ |
| | PMA | — | — |
| | LPS | — | — |
| HUVEC | none | +/– | +/– |
| | IL-1 | — | — |
| | IL-6 | — | — |
| | TNF-a | — | — |
| | PMA | — | — |
| | LPS | — | — |

PCR analysis of the indicated cell lines after co-culture with KS cell lines (KS-3 + KS-6) for KS herpesvirus
(A). Determination of PCR positivity and cytopathic effect (CPE) was performed with the indicated stimulus in 293 cells and HUVEC (B). For PCR, +++ denotes consistent and readily visible 233 bp product by ethidium bromide staining; + indicates weaker positivity; +/– indicates inconsistent detection.
For CPE, +++ indicates >80% nonviable cells by day 5, + by day 10–11, +/– inconsistent effects.

The cytopathic effect (CPE) was manifested by >80% cell death, with the presence of multi-nucleated giant cells, prominent chromatin condensation, and nuclear molding noted in the culture. This CPE was not observed after incubation of 293 with TNF-a in the absence of KS cells (data not shown). Finally, although a PCR signal had been observed on occasion in HUVEC, no consistent cytopathic effect was observed in these cells. We therefore focused our efforts on 293 cells as a host cell for viral replication.

Propagation of Virus by Serial Passage

To propagate the virus, cell-free lysates were prepared at different times after infection and incubated with 293 cells in the presence or absence of TNF-x. Although TNF-a enhanced viral replication during the primary KS/293 cell co-culture, it did not enhance CPE or viral titers during serial passage on 293 cells and was not used further. No PCR signal was detected in uninfected cells, but a signal was readily detected in infected 293 cells within 1 day after infection. PCR signals of viral DNA were maximal three days after viral challenge, and diminished on day five (FIG. 2A), when >80% of cells showed severe cytopathic effects (FIG. 3), possibly due to nonspecific degradation. The signal was detected more readily in the nuclear fraction, with a weaker signal present in the cytoplasm (FIG. 2B). Hirt supernatants of low molecular weight DNA from the nucleus were also found to contain the Kaposi's herpesvirus sequence by PCR (FIG. 2A). No PCR signal was detected from other known herpesviruses in serially passaged viral isolates, despite their ready detection in positive control tissues or cell lines infected with the relevant viruses (FIG. 4). To serially passage the virus, cell lysates were prepared on day 3–4, prior to the generation of CPE. The resultant cell lysates (day 3) conferred CPE and a positive PCR signal on uninfected 293 cells and was maintained consistently with titers $\pm 10^6$/ml for at least 5 serial passages.

Virus Filtration, Heat, Inactivation, and Detection of Viral DNA by Endpoint Dilution Analysis Cell-free lysates from the primary TNF-a stimulated co-cultures were prepared and incubated with fresh 293 cells in the absence of other cell types. Transfer of this cytopathic activity and detection of PCR signal after serial passage was maintained after filtration with a 0.4 mM filter, but was lost after heat inactivation of viral lysates (Table 3).

TABLE 3

| Treatment | CPE day post treatment | | | | |
|---|---|---|---|---|---|
| | 1 | 2 | 3 | 4 | 5 |
| cell free viral lysates | − | − | + | ++ | +++ |
| cell free viral lysates: heat activated | − | − | − | − | − |
| cell free viral lysates: filtered | − | − | + | ++ | +++ |

Determination of cytopathic effect (CPE) in 293 cells was performed after exposure to lysate subjected to the indicated treatments, and severity was graded as follows: −, +, ++, +++

293 cells were incubated with increasing dilutions of viral lysates, and cells were examined for CPE and viral sequences by PCR. As noted previously, CPE was observed at a lysate dilution of $10^{-6}$ but not $10^{-8}$. Infection of 293 cells and the development of CPE also correlated with the appearance of a detectable PCR signal for HHV-8. Viral DNA was also detectable by Southern blot hybridization during propagation. Quantitation of the Southern blot signal suggested a relatively low copy number of virus per cell (1–10 copies per genome).

Light Microscopic Analysis

To characterize the effects of viral infection further and document the presence of the virus after serial propagation, additional microscopic analyses were performed. Light microscopic analysis of the cytopathic effect was performed in one micron-thick plastic embedded toluidine-blue stained sections of 293 cells. Uninfected 293 cells revealed viable appearing epithelial cells with round nuclei containing evenly distributed chromatin and prominent nucleoli. In contrast, after exposure to the infected cell lysate, 293 cells, beginning as an early as day 2 demonstrated significant cytopathic changes. Infected 293 cells were characterized by the presence of multinucleated giant cells, nuclear molding, and dissolution of chromatin with residual chromatin marginating along the nuclear membrane (FIG. 5, A vs. B,C). By day 5, virtually all of the cells were undergoing necrosis with condensation of chromatin and other morphological changes consistent with apoptosis (FIGS. 3 and 5B,C).

Electron Microscopy of KS Cells and Infected 293 Cells

Initially, cultured KS cells were analyzed using transmission electron microscopy to visualize cells in greater detail and to detect the potential presence of virus. In these early passage cells, evidence of particles was found in the cytoplasm whose size and shape was consistent with that of a herpes virion (FIG. 1B, inset); however, particles were infrequent, and the morphology was not sufficient to identify the particle definitively as a herpesvirus. Additional studies were undertaken to characterize the virus particle propagated on 293 cells. Cells were examined daily after exposure to cell-free viral lysates. Virus particles were observed in the nucleus of infected cells as early as two days after infection.

REFERENCES

1. Beral, V., Peterman, T. A., Berkelman, R. L., and Jaffe, H. W. Kaposi's sarcoma among persons with AIDS: a sexually transmitted infection? Lancet, 335: 123–128, 1990.

2. Safai, B., Johnson, K. G., Myskowski, P. L., Koziner, B., Yang, S. Y., Cunningham-Rundles, S., Godbold, J. H., and Dupont, B. The natural history of Kaposi's sarcoma in the acquired immunodeficiency syndrome. Ann. Intern. Med. 103: 744–750, 1985.

3. Beral, V., Jaffe, H., and Weiss, R. Cancer surveys: cancer, HIV, and AIDS. Eur. J. Cancer. 27: 1057–1058, 1991.

4. Stein, M., Spencer, D., Kuten, A., and Bezwoda, W. AIDS-related Kaposi's sarcoma: a review. Isr. J. Med. Sci. 30: 298–305, 1994.

5. Finesmith, T. H. and Shrum, J. P. Kaposi's sarcoma. Int. J. Dermatol. 33: 755–762, 1994.

6. Ioachim, H. L., Adsay, V., Giancotti, F. R., Dorsett, B., and Melamed, J. Kaposi's sarcoma of internal organs. Cancer, 75: 1376–1385, 1995.

7. Nickoloff, B. J., Griffiths, C. E. M., Gallo, R. C., Salahuddin, S. Z., and Nakamura, S. Factor XIIIa-expressing dermal dendrocytes in AIDS-associated cutaneous Kaposi's sarcomas. Science, 243: 1736–1737, 1989.

8. Rutgers, J. F., Wieczorek, R., Bonetti, F., Kaplan, K. E., Posenett, D. N., Friedman-Kien, A. E., and Knowles, D. M. The expression of endothelial cell surface antigen by AIDS-associated Kaposi's sarcoma: evidence for a vascular endothelial cell origin. Am. J. Pathol. 122: 493–499, 1986.

9. Naidu, Y. M., Rosen, E. M., Zitnick, R., Goldberg, I., Park, M., Naujokas, M., Polverini, P. J., and Nickoloff, B. J. Role of scatter factor in the pathogenesis of AIDS-related Kaposi's sarcoma. Proc. Natl. Acad. Sci. USA, 91: 5281–5285, 1994.

10. Browning, P. J., Sechler, J. M., Kaplan, M., Washington, R. H., Gendelman, R., Yarchoan, R., Ensoli, B., and Gallo, R. C. Identification and culture of Kaposi's sarcoma-like spindle cells from the peripheral blood of human immunodeficiency virus-1-infected individuals and normal controls. Blood, 84: 2711–2720, 1994.

11. Samaniego, F., Markham, P. D., Gallo, R. C., and Ensoli, B. Inflammatory cytokines induce AIDS-Kaposi's sarcoma-derived spindle cells to produce and release basic fibroblast growth factor and enhance Kaposi's sarcoma-like lesion formation in nude mice. J. Immunol. 154: 3582–3592, 1995.

12. Ensoli, B., Barillari, G., and Gallo, R. C. Cytokines and growth factors in the pathogenesis of AIDS-associated Kaposi's sarcoma. Immunol. Rev. 127: 147–155, 1992.

13. Barillari, G., Buonaguro, L., Fiorelli, V., Hoffman, J., Michaels, F., Gallo, R. C., and Ensoli, B. Effects of cytokines from activated immune cells on vascular cell growth and HIV-1 gene expression. J. Immunol. 149: 3727–3734, 1992.

14. Ensoli, B., Gendelman, R., Markham, P., Fiorelli, V., Colombini, S., Raffeld, M., Cafaro, A., Chang, H. K., Brady, J. N., and Gallo, R. C. Synergy between basic fibroblast growth factor and HIV-1 Tat protein in induction of Kaposi's sarcoma. Nature, 371: 674–680, 1994.

15. Nair, B. C., DeVico, A. L., Nakamura, S., Copeland, T. D., Chen, Y., Patel, A., O'Neil, T., Oroszlan, S., Gallo, R. C., and Sarngadharan, M. G. Identification of a major growth factor for AIDS-Kaposi's sarcoma cells as oncostatin M. Science, 255: 1430–1432, 1992.

16. Beral, V. Epidemiology of Kaposi's sarcoma. Cancer Surv. 10: 5–22, 1991.

17. Chang, Y., Cesarman, E., Pessin, M. S., Lee, F., Culpepper, J., Knowles, D. M., and Moore, P. S. Identification of herpesvirus-like DNA sequences in AIDS-associated Kaposi's sarcoma. Science, 266: 1865–1869, 1994.

18. Huang, Y. Q., Li, J. J., Kaplan, M. H., Poiesz, B., Katabira, E., Zhang, W. C., Feinder, D., and Friedman-Kien, A. E. Human herpesvirus-like nucleic acid in various forms of Kaposi's sarcoma. Lancet, 345: 759–761, 1995.

19. Moore, P. S. and Chang, Y. Detection of herpes-like virus DNA sequences in Kaposi's sarcoma in patients with and without HIV infection. N. Eng. J. Med. 332: 1181–1185, 1995.

20. Ambroziak, J. A., Blackburn, D. J., Herndier, B. G., Glogau, R. G., Gullet, J. H., MacDonald, A. R., Lennette, E. T., and Levy, J. A. Herpes-llike sequences in HIV-infected and uninfected Kaposi's sarcoma patients. Science, 268: 582–583, 1995.

21. Cesarman, E., Chang, Y., Moore, P. S., Said, J. W., and Knowles, D. W. Kaposi's sarcoma-associated herpesvirus-like DNA sequences in AIDS-related body-cavity-based lymphomas. N. Eng. J. Med. 332: 1186–1191, 1995.

22. Cesarman, E., Moore, P. S., Rao, P. H., Inghirami, G., Knowles, D. M., and Chang, Y. In vitro establishment and characterization of two acquired immunodeficiency syndrome-related lymphoma cell lines (BC-1 and BC-2) containing Kaposi's sarcoma-associated herpesvirus-like (KSHV) DNA sequences. Blood, 86: 2708–2714, 1995.

23. Lebbe, C., de Cremoux, P., Rybojad, M., Costa da Cunha, C., Morel, P., and Calvo, F. Kaposi's sarcoma and new herpesvirus. Lancet, 345: 11801995.

24. Dupin, N., Grandadam, M., Calvez, V., Gorin, I., Aubin, J. T., Havard, S., Lamy, F., Leibowitch, M., Huraux, J. M., Escande, J. P., and Agut, H. Herpesvirus-like DNA sequences in patients with Mediterranean Kaposi's sarcoma. Lancet, 345: 761–762, 1995.

25. Whitby, D., Howard, M. R., Tenant-Flowers, M., Brink, N. S., Copas, A., Boshoff, C., Hatzioannou, T., Suggett, F. E., Aldam, D. M., Denton, A. S., Miller, R. F., Weller, I. V., Weiss, R. A., Tedder, R. S., and Schulz, T. F. Detection of Kaposi sarcoma associated herpesvirus in peripheral blood of HIV-infected individuals and progression to Kaposi's sarcoma. Lancet, 346: 799–802, 1995.

26. Levy, J. A. A new human herpesvirus: KSHV or HHV8? Lancet, 346: 7861995.

27. Cohen, J. Controversy: is KS really caused by new herpesvirus? Science, 268: 1847–1848, 1995.

28. Coen, D. M. Quantitation of rare DNAs by PCR. In: F. M. Ausubel, R. Brent, R. E. Kingston, D. D. Moore, J. G. Seidman, J. A. Smith and K. Struhl (eds.), Current Protocols in Molecular Biology, pp. 15.3.1–15.3.8, New York: Greene Publishing Associates and Wiley-Interscience. 1992.

29. Huang, Y. Q., Friedman-Kien, A. E., Li, J. J., and Nickoloff, B. J. Cultured Kaposi's sarcoma cell lines express Factor XIIIa, CD14, and VCAM-1, but not Factor VIII or ELAM-1. Arch. Dermatol. 129: 1291–1296, 1993.

30. Yang, J., Xu, Y., Zhu, C., Hagan, M. K., Lawley, T., and Offermann, M. K. Regulation of adhesion molecule expression in Kaposi's sarcoma cells. J. Immunol. 152: 361–373, 1994.

31. Jaffe, E. A. Culture and identification of large vessel endothelial cells. In: E. A. Jaffe (ed.), Biology of Endothelial Cells, pp. 1–3, the Hague: Martinus Nijoff. 1984.

32. Eizuru, Y., Inagawa, S., and Minamishima, Y. Application of "Hirt supernatant" DNA to the molecular epidemiology of cytomegalovirus infections. J. Clin. Microbiol. 20: 1012–1014, 1984.

33. Pater, M. M., Hyman, R. W., and Rapp, F. Isolation of herpes simplex virus DNA from the "Hirt supernatant". Virol. 75: 481–483, 1976.

34. Sa'Adu, A., Thomson, B. J., Bountiff, L., and Webster, A. D. Lymphotropic viruses in "common variable" immunodeficiency-PCR analysis of lymphocyte DNA for HIV-1 and HHV-6. Clin. Exp. Immunol. 91: 50–53, 1993.

35. Cao, M., Xiao, X., Egbert, B., Darragh, T. M., and Yen, T. S. Rapid detection of cutaneous herpes simplex virus infection with the polymerase chain reaction. J. Invest. Dermatol. 92: 391–392, 1989.

36. Apolloni, A. and Sculley, T. B. Detection of A-type and B-type Epstein-Barr virus in throat washings and lymphocytes. Virol. 202: 978–981, 1994.

37. Manthorpe, M., Cornefert-Jensen, F., Hartikka, J., Felgner, J., Rundell, A., Margalith, M., and Dwarki, V. Gene therapy by intramuscular injection of plasmid DNA: studies on firefly luciferase gene expression in mice. Hum. Gene Ther. 4: 419–431, 1993.

Having now fully described the invention, it will be apparent to one of ordinary skill in the art that many changes and modifications can be made thereto without departing from the spirit or scope of the invention as set forth herein.

---

What is claimed as new and is desired to be secured by Letters Patent of the United States is:

1. A method of cultivating KS cells according to the present invention comprises the steps of:

isolating a KS cell from a KS lesion or from tissue taken from a patient biopsy; and culturing said KS cell on a medium coated with endothelial cell attachment factor.

2. The method of claim 1, wherein said KS cell is taken from a KS lesion derived from a patient with AIDS.

3. The method of claim 1, wherein said medium is RPMI medium supplemented with antibiotics, serum and growth factors.

4. A method for propagating a cell infected with human herpesvirus 8 (HHV-8) comprising:

contacting a culture of epithelial cells or umbilical endothelial cord cells with a cell or cell lysate of a HHV-8 to form an infected cell culture, incubating the infected cell culture for at least 1 day, and passaging the infected cell culture.

5. The method of claim 4, wherein said epithelial cell is a embryonic epithelial cell.

6. The method of claim 5, wherein said embryonic epithelial cell is a human embryonic kidney epithelial cell.

7. The method of claim 5, wherein said human embryonic kidney epithelial cell is a 293 cell.

8. The method of claim 4, wherein the infected cell culture is incubated for at least 3 days prior to passaging.

9. A method of detecting the presence of human herpesvirus 8 (HHV-8) in a biological fluid comprising:

contacting said biological fluid from said patient with an antibody specific HHV-8, and detecting the presence of complexes of antibody and human herpesvirus.

10. The method of claim 9, wherein said biological fluid is blood, semen or urine.

11. A method of detecting the presence of antibodies selective for human herpesvirus 8 (HHV-8) in a biological fluid comprising:

contacting said biological fluid from said patient with HHV-8 viral antigen so as to form complexes between said viral antigen and any antibodies selective for HHV-8, detecting the presence of said complexes of antibody and viral antigen.

12. A method of screening for antiviral activity against human herpesvirus 8 (HHV-8), comprising:

cultivating a cell line infected with HHV-8 for at least 1 day, contacting said infected cell culture with an antiviral drug candidate to form an exposed cell culture, culturing the exposed cell in the presence of the antiviral drug candidate, and determining the effect of the antiviral drug candidate.

* * * * *

UNITED STATES PATENT AND TRADEMARK OFFICE
CERTIFICATE OF CORRECTION

PATENT NO. : 6,114,110
DATED : September 5, 2000
INVENTOR(S) : Gary J. Nabel et al.

It is certified that error appears in the above-identified patent and that said Letters Patent is hereby corrected as shown below:

Title page, column 1,
Line 11, under "OTHER PUBLICATIONS", change "Effect" to -- Effects --.

Column 2,
Line 11, change "Browing" to -- Browning --.

Page 2, column 1,
Line 55, under "OTHER PUBLICATIONS", change "Shor-Duration" to -- Short-Duration --.
Line 61, under "OTHER PUBLICATIONS", change "sarcoma, and" to -- sarcoma and --.

Page 2, column 2,
Line 36, change "Reene" to -- Renne --.

Page 3, column 2,
Line 3, change "progression ot" to -- progression to --.

Signed and Sealed this

Sixth Day of November, 2001

Attest:

NICHOLAS P. GODICI
Attesting Officer   Acting Director of the United States Patent and Trademark Office

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid -continued

```
            (A) DESCRIPTION: /desc = "primer"

(xi) SEQUENCE DESCRIPTION: SEQ ID NO:1:

AGCCGAAAGG ATTCCACCAT TGTGCTC                                              27

(2) INFORMATION FOR SEQ ID NO:2:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:2:

TCCGTGTTGT CTACGTCCAG ACGATAT                                              27

(2) INFORMATION FOR SEQ ID NO:3:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:3:

CCAAGCTTCC ACGCTGTTTT GACCTCCATA GA                                        32

(2) INFORMATION FOR SEQ ID NO:4:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:4:

CCAAGCTTCT GTCAGCTATT ATGTCTGGTG GC                                        32
```